United States Patent [19]

Neumann

[11] Patent Number: 4,588,725
[45] Date of Patent: May 13, 1986

[54] 2-PIPERAZINYL-QUINAZOLINE DERIVATIVES AND PHARMACEUTICAL COMPOSITIONS CONTAINING THEM

[75] Inventor: Peter Neumann, Berne, Switzerland

[73] Assignee: Sandoz Ltd., Basel, Switzerland

[21] Appl. No.: 550,909

[22] Filed: Nov. 10, 1983

[30] Foreign Application Priority Data

Nov. 12, 1982 [CH] Switzerland .................. 6614/82

[51] Int. Cl.[4] .................. A61K 31/505; C07D 403/08
[52] U.S. Cl. ........................... 514/254; 514/218; 260/243.3; 544/287; 544/292
[58] Field of Search .................. 544/292, 287, 251; 260/243.3; 514/218, 254

[56] References Cited

U.S. PATENT DOCUMENTS

| 3,435,036 | 3/1969 | Regmler et al. | 424/251 |
| 3,517,005 | 6/1970 | Cronin et al. | 544/292 |
| 3,585,193 | 6/1971 | Regnier et al. | 544/295 |
| 4,435,401 | 3/1984 | Campbell et al. | 544/295 |

FOREIGN PATENT DOCUMENTS

| 453892 | 11/1977 | Spain . |
| 1369379 | 10/1974 | United Kingdom . |
| 1553436 | 9/1979 | United Kingdom . |

OTHER PUBLICATIONS

Derwent Abstract 24377E/13.
Chem. Abstracts 89: 43492s, 1978.
Journal of Medicinal Chemistry, 1972, vol. 15, No. 3, pp. 295-301.

Primary Examiner—Richard L. Raymond
Assistant Examiner—James H. Turnipseed
Attorney, Agent, or Firm—Gerald D. Sharkin; Robert S. Honor; Joseph J. Borovian

[57] ABSTRACT

2-Piperazinyl-quinazolines or pharmaceutically acceptable acid addition salts thereof are useful as neuroleptic and anti-hypertensive agents.

9 Claims, No Drawings

2-PIPERAZINYL-QUINAZOLINE DERIVATIVES AND PHARMACEUTICAL COMPOSITIONS CONTAINING THEM

The present invention relates to 2-piperazinyl-quinazolines, their production and pharmaceutical compositions containing them.

The present invention provides 2-(N-Phenylalkyl-, -N-benzoylalkyl- or -N-phenoxyalkyl-piperazino- or -homopiperazino)-quinazolines and acid addition salts thereof, hereinafter referred to as compounds of the invention. It is to be appreciated that a compound of the invention may be optionally substituted in any available position, e.g. the phenylalkyl group may be substituted in the alkyl moiety by hydroxy.

The present invention in particular provides compounds of formula I,

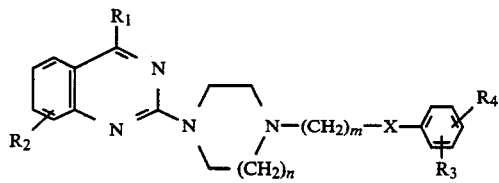

wherein
$R_1$ is hydrogen, $(C_{1-6})$alkyl, $(C_{3-7})$cycloalkyl or phenyl, the phenyl ring optionally being monosubstituted by halogen, $(C_{1-4})$alkyl or $(C_{1-4})$alkoxy, $R_2$ is hydrogen, halogen, hydroxy, $(C_{1-6})$alkyl, $(C_{1-4})$alkoxy or benzyloxy, n is 1 or 2, $R_3$ and $R_4$ are each, independently, hydrogen, halogen, $(C_{1-4})$alkyl, $(C_{1-4})$alkoxy, $(C_{2-4})$acyl or trifluoromethyl, and X is —$CH_2$— and m is 0, 1, 2 or 3, or X is —CHOH— and m is 2 or 3, or X is —CO— or a protected —CO— group and m is 1, 2 or 3, or X is —O— and m is 2 or 3, or X is a group of formula II,

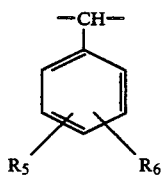

wherein $R_5$ and $R_6$ are each, independently, hydrogen, halogen, $(C_{1-4})$alkyl, $(C_{1-4})$alkoxy or trifluoromethyl and m is 3, and acid addition salts thereof.

Any alkyl radical of 1 to 6 carbon atoms is preferably of 1 to 4 carbon atoms, especially of 1 or 2 carbon atoms. Any alkyl or alkoxy radical of 1 to 4 carbon atoms is preferably of 1 to 3 carbon atoms, especially 1 or 2 carbon atoms. Halogen means fluorine, chlorine, bromine or iodine, preferably fluorine or chlorine. Acyl is especially acetyl. A suitable —CO— protecting group is for example a dialkylketal group such as dimethyl or diethyl ketal group or an alkylene ketal group such as ethylene or n-propylene ketal group.

Most suitably $R_3$ is attached para to the X moiety. $R_3$ is preferably halogen, especially fluorine. $R_4$ is preferably hydrogen or halogen. Suitably $R_5$ is attached para to the —CH— moiety. Conveniently $R_5$ is halogen, especially fluorine. Suitably X is —O— but more suitably X is —CO—. Particularly suitable values for m are 2 or 3 preferably 3. A preferred value for n is 1.

The present invention in another aspect provides a process for the production of a compound of the invention which comprises reacting an appropriate quinazoline having a leaving group in the 2 position with an appropriate N-phenylalkyl-, N-benzoylalkyl- or N-phenoxyalkyl-piperazine or -homopiperazine and recovering the resultant compound in free base form or in acid addition salt form.

In particular a compound of formula I as defined above may be produced by a process which comprises reacting a compound of formula III,

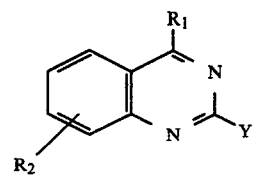

wherein $R_1$ and $R_2$ are as defined above, and Y is a leaving group, with a compound of formula IV,

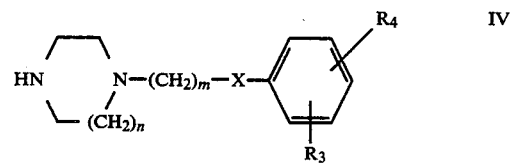

wherein $R_3$, $R_4$, X, m and n are as defined above, and recovering the compound of formula I in free base form or in acid addition salt form.

The process may be effected in conventional manner for analogous reactions.

The reaction of a quinazoline having a leaving group in the 2 position, in particular a compound of formula III, wherein the leaving group Y denotes for example $(C_{1-4})$alkoxy or $(C_{1-4})$alkylthio, p-nitrobenzylthio or preferably halogen, especially chlorine, is conveniently carried out in an inert organic solvent such as isopropanol, toluene, dimethylformamide or dimethylsulfoxide at a temperature in the range from 50° to 200° C., preferably 80° to 140° C. The reaction is conveniently carried out in the presence of an acid-binding agent, e.g. potassium carbonate, pyridine or triethylamine. An excess of N-phenylalkyl-, N-benzoylalkyl- or N-phenoxyalkyl-piperazine or -homopiperazine, in particular a compound of formula IV as acid-binding agent may also be used.

For the preparation of a 2-(N-benzoylalkyl-piperazino- or -homopiperazino)-quinazoline, in particular a compound of formula I, wherein X is —CO—, it may be convenient to protect the —CO— group in the starting material. Examples of such protecting groups are given above. The removal of such group can be effected in known manner.

The starting materials may be prepared in known manner.

Insofar as the production of starting materials is not particularly described these compounds are known or may be produced in analogous manner to known compounds or to processes described herein.

The compounds of the invention may be converted into acid addition salts thereof in conventional manner and vice versa. Suitable acid include for example, hydrochloric acid, hydrobromic acid, succinic acid, maleic acid or fumaric acid.

In the following examples all temperatures are given in degrees centigrade and are uncorrected.

EXAMPLE 1

4-[4-(Quinazolin-2-yl)-1-piperazinyl]-1-(4-fluorophenyl)-1-butanone 2.25 g 2-Chloroquinazoline, 4.2 g 1-(3-[2-(4-fluorophenyl)-1,3-dioxolan-2-yl]-propyl)piperazine and 2 ml triethylamine in 8 ml isopropanol are stirred and heated 2½ hours at 80° C. The solvent is then evaporated in vacuo and the residue is taken up in hexane. The hexane solution is treated with charcoal, filtered and concentrated whereby the ketal of the title compound crystallizes out. The resulting precipitate is dissolved in 40 ml aqueous 1N hydrochloric acid. After 1 hour the acidic solution is made alkaline with aqueous ammonia. The resulting precipitate is filtered off and recrystallized from ethyl acetate to give the title compound, m.p. 129°–131° C.

EXAMPLE 2

2-{4-[3-(4-Fluorophenoxy)propyl]-1-piperazinyl}quinazoline 2.5 g 2-Chloro-quinazoline, 3.8 g 1-[3-(4-fluorophenoxy)propyl]piperazine and 2.5 ml triethylamine in 15 ml isopropanol are stirred under reflux for 5 hours. The solvent is then evaporated in vacuo and the residue partitioned between water and methylene chloride. The organic phase is dried and evaporated. The residue is recrystallized from ethanol to yield the title compound, m.p. 126°–128° C.

EXAMPLE 3

In analogous manner to that disclosed in Example 1 or 2 the following compounds of formula I are produced, wherein n is 1 and m is 3:

| Example | $R_1$ | $R_2$ | X | $R_3$ | $R_4$ | m.p. °C. |
|---|---|---|---|---|---|---|
| a | methyl | H | CO | 4-F | H | 101–103 |
| b | i-propyl | H | CO | 4-F | H | 100.5–102 |
| c | n-butyl | H | CO | 4-F | H | 69.5–71.5 |
| d | cyclohexyl | H | CO | 4-F | H | 93–95 |
| e | phenyl | H | CO | 4-F | H | 120–122 |
| f | p-chlorophenyl | H | CO | 4-F | H | 103.5–105.5 |
| g | p-fluorophenyl | H | CO | 4-F | H | 102–105 |
| h | p-tolyl | H | CO | 4-F | H | 91–94 |
| i | p-methoxyphenyl | H | CO | 4-F | H | 99.5–103.5 |
| j | phenyl | 6-Cl | CO | 4-F | H | 143–145 |
| k | phenyl | 7-CH$_3$ | CO | 4-F | H | 129.5–131.5 |
| l | o-chlorophenyl | 6-Cl | CO | 4-F | H | 102–112 |
| m | p-chlorophenyl | 7-Cl | CO | 4-F | H | 165–168 |
| n | phenyl | H | CH–(4-F-C$_6$H$_4$) | 4-F | H | 142–144 |
| o | phenyl | H | CH(OH) | 4-F | H | >153 (decomp.) dihydrochloride |

EXAMPLE 4

In analogous manner to that disclosed in Example 1 or 2 the following compounds of formula I may be prepared:

| Ex. | $R_1$ | $R_2$ | m | n | X | $R_3$ | $R_4$ |
|---|---|---|---|---|---|---|---|
| a | H | 8-OC$_2$H$_5$ | 0 | 1 | CH$_2$ | 3-OC$_2$H$_5$ | 5-OC$_2$H$_5$ |
| b | H | 5-OH | 2 | 2 | O | 3-COC$_2$H$_5$ | H |
| c | H | 7-OCH$_2$C$_6$H$_5$ | 1 | 1 | CO | 2-CF$_3$ | 4-OCH$_3$ |
| d | n-C$_5$H$_{11}$ | H | 3 | 1 | CH–(3-CF$_3$-C$_6$H$_4$) | 3-Cl | 5-Cl |
| e | H | H | 3 | 1 | CH–(3-CH(CH$_3$)$_2$-C$_6$H$_4$) | H | H |
| f | H | H | 3 | 2 | CH–(3,5-(CH$_3$)$_2$-C$_6$H$_3$) | 4-Cl | H |

The compounds of the invention are useful because they possess pharmacological activity in animals and are therefore useful as pharmaceuticals, e.g. for therapy. In particular, the compounds of formula I are useful as neuroleptic agents in the treatment of e.g. psychotic disorders such as schizophrenia, as indicated in standard tests, e.g. by an inhibition of locomotion in mice. In this test groups of 3 male mice (18-24 g, OF-1, Sandoz Basle) received 3.2, 10, 32, 100 and 320 mg p.o. of the test drug. 1 hour after drug administration the mice were observed individually and their locomotion compared with that of control. The locomotion of the animals was observed and the $ED_{min}$ (the minimum dose at which significant inhibition was observed) determined. Values for representative compounds are given in the Table below.

The compounds of the invention bind further on $^3$H-spiperone binding sites in the brain [modified method of J. Leysen et al., Biochem. Pharmac. 27, 307 (1978)]. The test was performed as follows: fresh calf brain striatal tissue was homogenized in the 25 fold volume of tris buffer (pH 7.4, 50 mM, 120 mM sodium chloride) and centrifuged. The pellets were suspended in the 22 fold volume of tris buffer, incubated for 15 minutes at 37° C. and centrifuged. The pellets were suspended in the 300 fold volume of tris buffer. The composition of the assay mixtures was as follows: 45 mM tris buffer pH 7.7, 108 mM sodium chloride, membranes corresponding to 6 mg of original tissue weight, 0.1 nM $^3$H-spiperone, $5\times10^{-7}$M cinanserin to eliminate the contribution of 5-HT$_2$ receptors and 1 µM unlabelled spiperone for the determination of non-specific binding. To determine the inhibition of the specific binding of $^3$H-spiperone the test drugs were added to give 5 to 9 different concentrations between 1 nM and 10 µM, each in duplicate. After incubation for 40 minutes at room temperature, the assay mixtures were rapidly filtered through Whatman GF/B filter, the filters washed twice with 5 ml of ice cold tris buffer and scintillation-counted. The IC$_{50}$ values (concentration of a test drug which inhibits specific binding of $^3$H-spiperone by 50%) are determined by linear regression analysis. Values for representative compounds in the above tests are given below:

| Example | Locomotor inhibition $ED_{min}$ mg/kg p.o. | Receptor binding IC$_{50}$nM $^3$H—spiperone |
|---|---|---|
| 1 | 3.3 | 344 |
| 3e | <3.2 | 342 |
| clozapine | 3.2 | 990 |

Furthermore, the compounds on administration of 2-20 mg/kg p.o. to rats increase the sleep phase II and decrease the paradoxical sleep in the sleep/wake cycle carried out in accordance with the principles of H. Kleinlogel et al., European J. Pharmacol. 33, 159-163 (1975). Additionally the resulting sleep phase II shows a typical qualitative characteristics. Results obtained are e.g. as follows:

| Example | Dose mg/kg po | Sleep phase II % of control | paradoxical sleep % of control |
|---|---|---|---|
| 1 | 3.2 | 171 | 92 |
| 3e | 10 | 607 | 9 |
| clozapine | 10 | 483 | 26 |

For the above mentioned use the dosage will, of course, vary depending on the compound employed, mode of administration and therapy desired. However, in general, satisfactory results are obtained with a daily dosage of from about 0.1 mg to about 100 mg per kg animal body weight, conveniently given in divided doses 2 to 4 times a day or in sustained release form. For the larger mammals, the total daily dosage is in the range from about 25 mg to about 600 mg, and dosage forms suitable for oral administration comprise from about 6 mg to about 300 mg of the compounds admixed with a solid or liquid pharmaceutical carrier or diluent.

The compounds of the invention are furthermore useful as anti-hypertensive agents, as indicated in standard tests, for example in the $^3$H-Prazosin binding assay for $\alpha_1$-receptors [modified method of Greengrass P., et al., Eur. J. Pharmac. 55, 323-326 (1979)]. The test was performed as follows:

Fresh calf brain cortex tissue is homogenized in a 20 fold volume of Tris-HCl buffer (50 mM, pH 7.7), using a Polytron PT 20, and centrifuged at 30,000×g for 25 min. The pellets are resuspended in a 13 fold volume of the same buffer, incubated for 15 min at 37° C., and recentrifuged at 50,000×g for 11 min. The pellets of this centrifugation are frozen at −20° C. and resuspended in a 60 fold volume of the same buffer as above before use for the binding experiment. The composition of the assay mixtures (total volume=2 ml) is as follows: 50 mM Tris-HCl pH 7.7, membranes corresponding to 30 mg of original tissue weight, and 0.3 nM $^3$H-Prazosin. The assays for the definition of nonspecific binding additionally contain phentolamine at a concentration of 10 µM. To assess the potency of drugs in inhibiting specific $^3$H-Prazosin binding (difference between total and nonspecific binding), the test compounds are added to give 5 to 9 different concentrations between 1 nM and 10 µM, each in duplicate. After incubation for 40 min at room temperature, the assay mixtures are rapidly filtered through Whatman GF/B filters and washed twice with 5 ml of ice cold Tris buffer. The radioactivity of the filters is estimated by scintillation counting. For example the IC$_{50}$ of the Example 3a compound is 3.5 nM.

In another test female normotonic rats (200–350 g, Sprague-Dawley, Süddeutsche Tierfarm, Tuttlingen, FRG) were anaesthetized with urethane (1.5–1.75 g/kg i.p. in 2 portions) and a tracheal cannula was inserted. Blood pressure and heart rate were recorded from the carotid artery by conventional methods. Test drugs were administered by the jugular or the femoral vein. Body temperature was maintained at 34° C. by means of a temperature regulator (Alfos MK-4) triggered by a thermistor on the animal. After adaptation, increasing doses of the test drug were injected i.v. to give the following cumulative doses: 3, 13, 43, 143, 343 and 1443 µg/kg. ED 75% is the dose required to reduce the blood pressure or the heart rate to 75% of pretreatment values. It was obtained through interpolation. The ED$_{75}$ of the Example 3a compound is 524 µg/kg i.v.

For this use the dosage will, of course, vary depending on the compound employed, mode of administration and condition to be treated. However, in general, satisfactory results are obtained with a daily dosage of from about 0.01 to about 30 mg per kg animal body weight, conveniently given in divided doses 2 to 4 times a day, or in sustained release form. For the larger mammals the total daily dosage is in the range from about 5 to about 100 mg and dosage forms suitable for oral administration comprise from about 1 to about 50 mg of the compound admixed with a solid or liquid pharmaceutical carrier or diluent.

The compounds of the invention may be administered in similar manner to known standards for use in the above-mentioned utilities, for example, for the neuroleptic activity, Clozapine. The suitable daily dosage for a particular compound will depend on a number of factors such as its relative potency of activity. It has for example been determined that the preferred compounds of this invention, the Example 1 and Example 3e compounds, produce stronger effects in the $^3$H-spiperone binding test than Clozapine. This indicates that the compounds of Examples 1 and 3e may be administered at similar or lower dosages to that of Clozapine for the neuroleptic indication.

The compounds of the invention may be administered as the pharmaceutically acceptable acid addition salt thereof. Such acid addition salts exhibit the same order of activity as the free base forms. The present invention also provides a pharmaceutical composition comprising a compound of the invention or a pharmaceutically acceptable acid addition salt thereof, in association with a pharmaceutical carrier or diluent. Such compositions may be in the form of, for example, a solution or a tablet.

The neuroleptic activity is the preferred indication for the compounds of the invention. In this indication the preferred compounds are the Example 1 and 3e compounds.

In one group of compounds of formula I $R_1$ is hydrogen, $(C_{1-6})$alkyl or unsubstituted phenyl, $R_2$ is hydrogen, halogen, hydroxy, $(C_{1-6})$alkyl, $(C_{1-4})$alkoxy or benzyloxy, n is 1 or 2, $R_3$ and $R_4$ are each, independently, hydrogen, halogen, $(C_{1-4})$alkyl, $(C_{1-4})$alkoxy, $(C_{2-4})$acyl or trifluoromethyl and X is —CH$_2$— and m is 0, 1, 2 or 3, or X is —CO— or a protected —CO— group and m is 1, 2 or 3, or X is —O— and m is 2 or 3 and acid addition salts thereof.

Another group of compounds comprises compounds of formula I wherein $R_1$ is hydrogen, $(C_{1-6})$alkyl, $(C_{3-7})$cycloalkyl or phenyl, the phenyl ring optionally being monosubstituted by halogen, $(C_{1-4})$alkyl or $(C_{1-4})$alkoxy, $R_2$ is hydrogen, halogen or $(C_{1-6})$alkyl, n is 1, $R_3$ is halogen, $R_4$ is hydrogen, X is —CHOH— and m is 3, or X is —CO— and m is 3, or X is —O— and m is 3, or X is a group of formula II, wherein $R_5$ is halogen, $R_6$ is hydrogen and m is 3, and acid addition salts thereof.

In a first group of compounds $R_1$ is hydrogen.
In a second group of compounds $R_1$ is $(C_{1-6})$alkyl.
In a third group of compounds $R_1$ is $(C_{3-7})$cycloalkyl.
In a fourth group of compounds $R_1$ is phenyl.
In a fifth group of compounds $R_2$ is hydrogen.
In a sixth group of compounds $R_2$ is halogen.
in a seventh group of compounds $R_2$ is hydroxy.
In an eighth group of compounds $R_2$ is $(C_{1-6})$alkyl.
In a ninth group of compounds $R_2$ is $(C_{1-4})$alkoxy.
In a tenth group of compounds $R_2$ is benzyloxy.
In an eleventh group of compounds n is 1.
In a twelfth group of compounds $R_3$ is halogen.
In a thirteenth group of compounds $R_4$ is hydrogen.
In a fourteenth group of compounds X is —CH$_2$—.
In a fifteenth group of compounds x is —CHOH—.
In a sixteenth group of compounds X is —CO—.
In a seventeenth group of compounds X is —O—.
In an eighteenth group of compounds X is a group of formula II.
In a nineteenth group of compounds $R_5$ is halogen.
In a twentieth group of compounds $R_6$ is hydrogen.

What we claim is:
1. A compound of formula I,

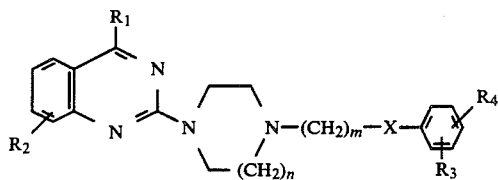

wherein
$R_1$ is hydrogen, $(C_{1-6})$alkyl, $(C_{3-7})$cycloalkyl or phenyl, the phenyl ring optionally being monosubstituted by halogen, $(C_{1-4})$alkyl or $(C_{1-4})$alkoxy,
$R_2$ is hydrogen, halogen, hydroxy, $(C_{1-6})$alkyl, $(C_{1-4})$alkoxy or benzyloxy,
n is 1 or 2,
$R_3$ and $R_4$ are each, independently, hydrogen, halogen, $(C_{1-4})$alkyl, $(C_{1-4})$alkoxy, $(C_{2-4})$acyl or trifluoromethyl, and
X is —CH$_2$— and m is 0, 1, 2 or 3, or
X is —CHOH— and m is 2 or 3, or
X is —CO— or a protected —CO— group and m is 1, 2 or 3, or
X is —O— and m is 2 or 3, or
X is a group of formula II,

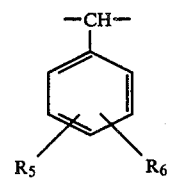

wherein $R_5$ and $R_6$ are each, independently, hydrogen, halogen, $(C_{1-4})$alkyl, $(C_{1-4})$alkoxy or trifluoromethyl and m is 3, or a pharmaceutically acceptable acid addition salt thereof.

2. A compound of claim 1 wherein $R_1$ is hydrogen, $(C_{1-6})$alkyl or unsubstituted phenyl, $R_2$ is hydrogen, halogen, hydroxy, $(C_{1-6})$alkyl, $(C_{1-4})$alkoxy or benzyloxy, n is 1 or 2, $R_3$ and $R_4$ are each, independently, hydrogen, halogen, $(C_{1-4})$alkyl, $(C_{1-4})$alkoxy, $(C_{2-4})$acyl or trifluoromethyl and X is —CH$_2$— and m is 0, 1, 2 or 3, or X is —CO— or a protected —CO— group and m is 1, 2 or 3, or X is —O— and m is 2 or 3, or a pharmaceutically acceptable acid addition salt thereof.

3. A compound of claim 1 wherein $R_1$ is hydrogen, $(C_{1-6})$alkyl, $(C_{3-7})$cycloalkyl or phenyl, the phenyl ring optionally being monosubstituted by halogen, $(C_{1-4})$alkyl or $(C_{1-4})$alkoxy, $R_2$ is hydrogen, halogen or $(C_{1-6})$alkyl, n is 1, $R_3$ is halogen, $R_4$ is hydrogen, X is —CHOH— and m is 3 or X is —CO— and m is 3, or X is —O— and m is 3, or X is a group of formula II, wherein $R_5$ is halogen, $R_6$ is hydrogen and m is 3, or a pharmaceutically acceptable acid addition salt thereof.

4. A compound of claim 1 which is 4-[4-(quinazolin-2-yl)-1-piperazinyl]-1-(4-fluorophenyl)-1-butanone, or a pharmaceutically acceptable acid addition salt thereof.

5. A compound of claim 1 which is 4-[4-(4-phenylquinazolin-2-yl)-1-piperazinyl]-1-(4-fluorophenyl)-1-butanone, or a pharmaceutically acceptable acid addition salt thereof.

6. A compound of claim 1 which is 4-[4-(4-n-butylquinazolin-2-yl)-1-piperazinyl]-1-(4-fluorophenyl)-1-butanone, or a pharmaceutically acceptable acid addition salt thereof.

7. A pharmaceutical composition comprising a pharmaceutically acceptable carrier or diluent and a therapeutically effective amount of a compound of claim 1, or a pharmaceutically acceptable acid addition salt thereof.

8. A method of treating schizophrenia which comprises administering a therapeutically effective amount of a compound of claim 1 or a pharmaceutically acceptable acid addition salt thereof to a subject in need of such treatment.

9. A method of treating schizophrenia which comprises administering a therapeutically effective amount of a compound of claim 5 or a pharmaceutically acceptable acid addition salt thereof to a subject in need of such treatment.

* * * * *